United States Patent [19]
Yamamoto et al.

[11] Patent Number: 5,639,920
[45] Date of Patent: Jun. 17, 1997

[54] PROCESS OF PRODUCING HYDROXYALKANAL

[75] Inventors: Hiroshi Yamamoto; Hisakazu Shindou, both of Suita; Tadahiro Yoneda, Ibaragi, all of Japan

[73] Assignee: Nippon Shokubai Co., Ltd., Osaka, Japan

[21] Appl. No.: 560,715

[22] Filed: Nov. 20, 1995

[30] Foreign Application Priority Data

Nov. 22, 1994 [JP] Japan .................................. 6-288307

[51] Int. Cl.$^6$ .................................................. C07C 45/61
[52] U.S. Cl. .................... 568/491; 568/861; 568/862; 568/465
[58] Field of Search .............................. 568/861, 465, 568/491

[56] References Cited

U.S. PATENT DOCUMENTS

| | | | |
|---|---|---|---|
| 2,434,110 | 1/1948 | Hatch et al. | 260/602 |
| 3,536,763 | 10/1970 | Eleuterio et al. | 260/602 |
| 5,015,789 | 5/1991 | Arntz et al. | 568/862 |
| 5,093,537 | 3/1992 | Unruh et al. | 568/862 |
| 5,171,898 | 12/1992 | Arntz et al. | 568/862 |
| 5,276,201 | 1/1994 | Haas et al. | 568/491 |
| 5,284,979 | 2/1994 | Haas et al. | 568/491 |

*Primary Examiner*—C. Warren Ivy
*Assistant Examiner*—S. Padmanashan
*Attorney, Agent, or Firm*—Kubovcik & Kubovcik

[57] ABSTRACT

In a process of producing hydroxyalkanal, a raw material, namely, an unsaturated aldehyde, is hydrated with a solution in the presence of a catalyst, and alcohol is added to the solution. A adding amount of the alcohol with respect to the unsaturated aldehyde is preferably in a range between 0.001 percent by weight and 10 percent by weight. According to this process, a consecutive reaction (side reaction) of a reaction product, namely, hydroxyalkanal, is curbed by the alcohol added to the solution, thereby making it possible to produce hydroxyalkanal at high selectivity out of a high-density unsaturated aldehyde solution. Therefore, the above process can trigger a reaction of an industrially advantageous unsaturated aldehyde solution, and thus improves the yield of hydroxyalkanal.

11 Claims, No Drawings

PROCESS OF PRODUCING HYDROXYALKANAL

FIELD OF THE INVENTION

The present invention relates to a process of producing hydroxyalkanal by hydrating an unsaturated aldehyde with a solution in the presence of a catalyst.

BACKGROUND OF THE INVENTION

In conventional processes, an unsaturated aldehyde, namely, acrolein, is hydrated with a solution in the presence of a catalyst to obtain hydroxyalkanal, namely, 3-hydroxypropanal(3-hydroxypropionaldehyde), which will be explained in the following paragraphs.

U.S. Pat. No. 2,434,110 discloses a process, in which a mineral acid, such as a sulfuric acid, is used as a homogeneous acid catalyst for the above reaction step. However, 3-hydroxypropanal retains low selectivity in this process, and thus is not produced efficiently. In addition, neither 3-hydroxypropanal is readily separated from the homogeneous catalyst, nor can the catalyst can be re-used easily.

To eliminate such a drawback, processes for improving the selectivity of 3-hydroxypropanal are proposed in the undermentioned publications.

U.S. Pat. No. 3,536,763 discloses a process, in which an acid ion exchange resin is used as an heterogeneous acid catalyst for the above reaction step.

U.S. Pat. No. 5,015,789 and U.S. Pat. No. 5,171,898 disclose processes, in which an ion exchange resin containing a phosphonate group, an amino group, or an aminophosphate group is used as a heterogeneous acid catalyst for the above reaction step.

U.S. Pat. No. 5,093,537 discloses a process, in which alumina bonding zeolite is used as a heterogeneous acid catalyst for the above reaction step.

U.S. Pat. No. 5,276,201 discloses a process, in which $TiO_2$ carrying a phosphoric acid is used as a heterogenous acid catalyst for the above reaction step.

Also, U.S. Pat. No. 5,284,979 discloses a process, in which the above reaction step is performed using a buffer solution containing a carboxylic acid and tertiary amine in the presence of an acid catalyst.

If a resulting solution of the raw material, acrolein, has low density (i.e., lower than 20 percent by weight), 3-hydroxypropanal retains satisfactory selectivity, thereby making it possible to obtain 3-hydroxypropanal at high selectivity by the above processes.

However, the inventors of the present invention found that when an industrially advantageous high-density acrolein solution (i.e., 20 or more percent by weight) is used for the reaction in each of the above processes, the reaction product, 3-hydroxypropanal, triggers an active consecutive reaction (side reaction) because it has an aldehyde group.

In other words, the above processes have a drawback that the selectivity from acrolein to 3-hydroxypropanal, and hence the selectivity of 3-hydroxypropanal is reduced. Therefore, increasing the density of the acrolein solution does not improve the yield of 3-hydroxypropanal by the above processes, indicating that these processes are not satisfactory in terms of industrial use.

SUMMARY OF THE INVENTION

It is therefore an object of the present invention to provide a process capable of solving the problems caused by conventional processes, and of producing hydroxyalkanal at high selectivity out of an industrially advantageous high-density unsaturated aldehyde solution.

To fulfil the above object, the inventors of the present invention performed experiments of processes for producing hydroxyalkanal by hydrating an unsaturated aldehyde with a solution in the presence of a catalyst, and found that the consecutive reaction of hydroxyalkanal was curbed when alcohol was added to the reaction solution. That is to say, the gist of the present invention is adding alcohol to the reaction solution, and the effect thereof is that hydroxyalkanal can be produced at high selectivity out of an industrially advantageous high-density unsaturated aldehyde solution.

In other words, to solve the above problems, a process of producing hydroxyalkanal in accordance with the present invention comprising a step of hydrating an unsaturated aldehyde with a solution in the presence of a catalyst promoting a hydration reaction is characterized in that alcohol is added in the above step.

The present invention is explained more in detail in the following paragraphs.

An unsaturated aldehyde (2-alkenal) used as a raw material in the present invention is not especially limited. However, a preferable unsaturated aldehyde is expressed by Formula (I) below, where R represents a substitutional group composed of either a hydrogen atom or hydrocarbon group having up to five carbons. The hydrocarbon group is a methyl group, an ethyl group, a propyl group, a butyl group, or an amyl group.

Examples of the above unsaturated aldehyde are: acrolein, methacrolein, 2-formyl-1-butene, 2-formyl-1-pentene, 2-formyl-1-hexene, 2-formyl-1-heptene, and the like. Of all these examples, a preferable unsaturated aldehyde is acrolein.

According to the process in accordance with the present invention, either 2-hydroxyalkanal or 3-hydroxyalkanal is selectively obtained from these examples. More precisely, in case of acrolein whose substitutional group represented by R in Formula (I) is a hydrogen atom, 3-hydroxyalkanal, namely, 3-hydroxypropanal (3-hydroxypropionaldehyde) is selectively obtained. In case of an unsaturated aldehyde whose substitutional group represented by R in Formula (I) is a hydrocarbon group, 2-hydroxyalkanal is selectively obtained. Note that 3-hydroxypropanal, obtained when acrolein is used as the unsaturated aldehyde, is an industrially important raw material of 1,3-propanediol.

The density of the unsaturated aldehyde solution (hereinafter referred to as the density) is, although it depends on the solubility of the unsaturated aldehyde to water, reaction temperature, etc., preferably in a range between 5 percent by weight and saturation, more preferably in a range between 5 percent by weight and 50 percent by weight, further preferably in a range between 20 percent by weight and 50 percent by weight, and most preferably in a range between 25 percent by weight and 40 percent by weight. A density lower than 5 percent by weight is not preferable because the yield of hydroxyalkanal is reduced. The density exceeding the saturation is not preferable either because an undissolved unsaturated aldehyde triggers a polymerization reaction or the like, and thus reduces the selectivity to hydroxyalkanal.

A catalyst used in the present invention is not especially limited, and any catalyst which can promote a hydration reaction of the unsaturated aldehyde will do. Examples of the catalyst are: (1) heterogeneous catalysts, such as an ion exchange resin, a (meta)acrylic acid-(meta)acrylamid copolymer, and solid non-organic materials and (2) homogeneous catalysts, such as a mineral acid, an acid-base buffer solution, and an organic acid including a (meta)acrylic acid and an acetic acid. One or more than one of these catalysts are used. Note that an amount of the catalyst with respect to the unsaturated aldehyde is not especially limited, and it can be adjusted depending on the kind of the catalyst. Also, a process of producing the catalyst is not especially limited.

Alcohol added to the reaction solution of the present invention is not especially limited. Either monohydric alcohol or polyhydric alcohol will do and a preferable alcohol is a dihydric. Examples of the alcohol are: ethylene glycol, 1,3-propanediol, 2-methyl-1,2-propanediol, 2-methyl-1,2-butanediol, 2-methyl-1,2-pentanediol, 2-methyl-1,2-hexanediol, 2-methyl-1,2-heptanediol, and the like.

In case that acrolein is used as the unsaturated aldehyde, a preferable alcohol is 1,3-propanediol which can be derived from a resulting product, 3-hydroxypropanal. More precisely, in case that acrolein is hydrated to synthesize 3-hydroxypropanal and the resulting 3-hydroxypropanal is hydrogenated to produce 1,3-propanediol, if the resulting 3-hydroxypropanal contains alcohol, namely, 1,3-propanediol, the 1,3-propanediol need not be separated from the 3-hydroxypropanal.

In case that methacrolein is used as the unsaturated aldehyde, a preferable alcohol is 2-methyl-1,2-propanediol for the same reason as above.

An adding amount of alcohol with respect to the unsaturated aldehyde is, although it depends on the kinds of alcohol, preferably in a range between 0.001 percent by weight and 10 percent by weight, more preferably in a range between 0.01 percent by weight and 5 percent by weight, further preferably in a range between 0.1 percent by weight and 2 percent by weight, and most preferably in a range between 1 percent by weight and 2 percent by weight. An adding amount of less than 0.001 percent by weight is not preferable because it is insufficient to realize the effect of adding alcohol. An adding amount exceeding 10 percent by weight is not preferable either because the yield of hydroxyalkanal is reduced.

The reason why adding alcohol, even in a slightest amount, brings excellent function and effect in the reaction in producing hydroxyalkanal out of an unsaturated aldehyde is not apparent. However, adding alcohol to the reaction solution is assumed to curb the consecutive reaction (side reaction) of the reaction product, hydroxyalkanal.

A reaction temperature is not especially limited, but a preferable range is between 50° C. and 250° C. In case that acrolein is used as the unsaturated aldehyde, a preferable range is between 50° C. and 140° C. A reaction temperature below 50° C. is not economically preferable because a reaction speed is decreased and a hydration reaction takes a long time. A reaction temperature exceeding 250° C. is not preferable either because the yield of hydroxyalkanal is reduced.

The present invention can be performed in a batch, semi-batch, or continuous manner, but in any case, a closed vessel is preferred for the reaction step. A reaction pressure inside the closed vessel is not especially limited, but a preferable range is between 1 kg/cm$^2$ and 20 kg/cm$^2$.

In case that a reaction takes place below the boiling point of the unsaturated aldehyde, it is preferable to apply a reaction pressure in a range between 1 kg/cm$^2$ and 5 kg/cm$^2$ to the reaction vessel by taking a vaporization pressure of the unsaturated aldehyde and other ingredients into consideration.

The above reaction pressure is applied, for example, by filling an inert gas ($N_2$ gas, He gas, etc.) into a reaction vessel. The higher the reaction pressure, the more the unsaturated aldehyde dissolves in water and the higher the yield of hydroxyalkanal becomes. On the other hand, the anti-pressure structure of a reaction vessel must be reinforced, which increases the size of the vessel undesirably. Thus, when setting a reaction pressure, these factors must be taken into consideration.

When the reaction ends, a hydroxyalkanal solution containing the added alcohol can be readily obtained by a simple separation process, such as filtration and distillation. A solution containing only an object product, hydroxyalkanal, can also be readily obtained. Further, hydroxyalkanal can be separated from the solution if so desired.

In case of 3-hydroxyalkanal of hydroxyalkanals, it may exist in the form of a hemiacetal and an acetal in the solution, but they can be easily converted into 3-hydroxyalkanal.

Likewise, hydroxyalkanal, in the presence of alcohol, may exist in the form of a hemiacetal and an acetal of the corresponding alcohol, but they can be easily converted into hydroxyalkanal.

Further, a carboxylic acid may be added to the reaction solution of the present invention. The kind of the carboxylic acid is not especially limited, and either a monatomic carboxylic acid or polyatomic carboxylic acid will do. Examples of the carboxylic acid are: (1) a monatomic carboxylic acid, such as a formic acid, an acetic acid, a (meta)acrylic acid, and (2) a diatomic carboxylic acid, such as an oxalic acid. Of all these examples, a polyatomic carboxylic acid, in particular, a diatomic carboxylic acid, such as oxalic acid, is preferred.

An adding amount of the carboxylic acid to the reaction solution with respect to the unsaturated aldehyde is, although it depends on the kinds of the unsaturated aldehyde and carboxylic acid, preferably in a range between 0.01 percent by weight and 10 percent by weight, more preferably in a range between 0.01 percent by weight and 5 percent by weight, and most preferably in a range between 0.01 percent by weight and 3 percent by weight. An adding amount less than 0.01 percent by weight is not preferable because it is not sufficient to realize the effect of adding the carboxylic acid. An adding amount exceeding 10 percent by weight is not preferable either because the yield of hydroxyalkanal is reduced.

According to the above process, the consecutive reaction (side reaction) of the reaction product, hydroxyalkanal, is curbed by adding alcohol to the reaction solution. Therefore, even when a high-density unsaturated aldehyde solution is used, hydroxyalkanal can be produced at high selectivity. In other words, the above process is suitable for producing hydroxyalkanal because it can use an industrially advantageous high-density unsaturated aldehyde solution, and thus improves the yield of hydroxyalkanal.

Hereinafter, the present invention is illustrated by the following examples of a preferred embodiment in comparison with comparative examples not according to the invention. However, the present invention is not limited to the undermentioned examples. Note that an invert ratio of the unsaturated aldehyde and the selectivity of the resulting hydroxyalkanal are defined as follows:

(1) An invert ratio of unsaturated aldehyde (%)=(the mole number of consumed unsaturated aldehyde/the mole number of supplied unsaturated aldehyde)×100

(2) Selectivity of hydroxyalkanal (%)=(the mole number of unsaturated aldehyde converted into hydroxyalkanal/the mole number of consumed unsaturated aldehyde)×100

(3) Selectivity of dimerized hydroxyalkanal=(the mole number of unsaturated aldehyde converted into dimerized hydroxyalkanal/the mole number of consumed unsaturated aldehyde)×100.

The amounts of the unsaturated aldehyde, hydroxyalkanal, and dimerized hydroxyalkanal are measured in any known manner, and gas chromatography (GC), one of known methods, is used in the present invention.

Other objects and advantages of the present invention will become apparent from the detailed description to follow taken in conjunction with the appended claims.

DESCRIPTION OF THE EMBODIMENT

First Example

A predetermined amount of water is poured into a reaction vessel equipped with a thermometer, a stirring instrument, and the like, and a predetermined amount of acrolein is also poured into the reaction vessel, so that the density of the resulting solution is 17 percent by weight.

Next, a predetermined amount of an ion exchange resin serving as a catalyst is added to the solution. Note that the ion exchange resin carries lead (Pb). Further, alcohol, namely, 1,3-propanediol, is added to the above solution in 1.3 percent by weight with respect to the above acrolein. "Duolite" of Rohm & Haas Co. is used as the ion exchange resin.

"Duolite" is an ion exchange resin of a macroporous structure containing an aminophosphate group as its functional group and a styrene-divinylbenzene copolymer as its host. "Duolite" used herein has an apparent specific gravity of 750 g/l and a particle size distribution of 10–50 mesh. An amount of lead carried by the resin is kept equal to or lower than a predetermined level, namely, not more than 5 percent by weight.

The above reaction solution is subject to reaction for three hours with stirring at 60° C. to hydrate acrolein. When the reaction ends, the resulting reaction solution is filtered, and analyzed in a predetermined manner, the results of which are set forth below.

(1) invert ratio of acrolein: 60%

(2) selectivity of 3-hydroxypropanal: 87%

(3) selectivity of dimerized 3-hydroxypropanal: 12%

(4) selectivity of hydroxyalkanal: 99% (total of (3) and (4))

There is produced a solution containing 8.1 percent by weight of 3-hydroxypropanal and 1.3 percent by weight of dimerized 3-hydroxypropanal obtained as the result of the above hydration reaction. A known raney nickel catalyst is added to the resulting solution to hydrogenate 3-hydroxypropanal and dimerized 3-hydroxypropanal. Reaction conditions are: a hydrogen pressure of 100kg/cm$^2$, a reaction temperature of 60° C., and reaction time of six hours.

When the reaction ends, the resulting solution is analyzed and it is acknowledged that there is produced 1,3-propanediol in an amount equal to a total of 3-hydroxypropanal and dimerized 3-hydroxypropanal. In other words, a predetermined amount of 1,3-propanediol is produced. This indicates that dimerized 3-hydroxypropanal is converted into 1,3-propanediol by a known hydrogenation process.

Second Example

An analysis is conducted in the same manner as the first example except that the density of the unsaturated aldehyde, namely, acrolein, is increased to 29 percent by weight from 17 percent by weight, and a reaction time is prolonged to four hours from three hours, the results of which are set forth below.

(1) invert ratio of acrolein: 40%

(2) selectivity of 3-hydroxypropanal: 67%

(3) selectivity of dimerized 3-hydroxypropanal: 19%

(4) selectivity of hydroxyalkanal: 86% (total of (3) and (4))

Third Example

An analysis is conducted in the same manner as the first example except that an adding amount of 1,3-propanediol is increased from 1.3 percent by weight to 5 percent by weight, and a reaction time is increased to 3.1 hours, the results of which are set forth below.

(1) invert ratio of acrolein: 76%

(2) selectivity of 3-hydroxypropanal: 82%

(3) selectivity of dimerized 3-hydroxypropanal: 12%

(4) selectivity of hydroxyalkanal: 94% (total of (3) and (4))

Fourth Example

An analysis is conducted in the same manner as the first example except that the density of acrolein is increased to 28 percent by weight from 17 percent by weight, a reaction temperature is increased to 90° C., a reaction time is reduced to two hours, and a DAET-based resin is used as a catalyst, the results of which are set forth below. Note that no lead is carried by the DAET-based resin.

(1) invert ratio of acrolein: 62%

(2) selectivity of 3-hydroxypropanal: 76%

(3) selectivity of dimerized 3-hydroxypropanal: 11%

(4) selectivity of hydroxyalkanal: 87% (total of (3) and (4))

The DAET-based resin is a copolymer of monomers: acrylic acid and diallylamineethanethiol and 1 percent by weight of divinylbenzene is used as a crosslinking agent in producing the above copolymer.

Fifth Example

An analysis is conducted in the same manner as the fourth example except that an adding amount of 1,3-propanediol is increased to 11.3 percent by weight from 1.3 percent by weight, the results of which are set forth below.

(1) invert ratio of acrolein: 63%

(2) selectivity of 3-hydroxypropanal: 64%

(3) selectivity of dimerized 3-hydroxypropanal: 10%

(4) selectivity of hydroxyalkanal: 74% (total of (3) and (4))

First Comparative Example

An analysis is performed in the same manner as the first example except that alcohol, namely, 1,3-propanediol, is not used, the results of which are set forth below.

(1) invert ratio of acrolein: 55%

(2) selectivity of 3-hydroxypropanal: 79%

(3) selectivity of dimerized 3-hydroxypropanal: 10%

(4) selectivity of hydroxyalkanal: 89% (total of (3) and (4))

Second Comparative Example

An analysis is performed in the same manner as the second example except that alcohol, namely, 1,3-propanediol, is not used and the reaction times is cut to three hours, the results of which are set forth below.

(1) invert ratio of acrolein: 43%

(2) selectivity of 3-hydroxypropanal: 59%

(3) selectivity of dimerized 3-hydroxypropanal: 15%

(4) selectivity of hydroxyalkanal: 74% (total of (3) and (4))

It should be noted that there is also produced an abundance of products caused by the consecutive reaction of 3-hydroxypropanal.

Third Comparative Example

An analysis is performed in the same manner as the fourth example except that 1,3-propanediol is omitted, the results of which are set forth below.

(1) invert ratio of acrolein: 61%

(2) selectivity of 3-hydroxypropanal : 72%

(3) selectivity of dimerized 3-hydroxypropanal: 11%

(4) selectivity of hydroxyalkanal: 83% (total of (3) and (4))

The above results reveal that, in the process of each of the examples in accordance with the embodiment of the present invention, adding 1,3-propanediol to a reaction solution curbs the consecutive reaction of the reaction product, 3-hydroxypropanal, thereby making it possible to produce 3-hydroxypropanal at high selectivity out of a high-density acrolein solution.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process of producing hydroxyalkanal comprising a reaction step of producing hydroxyalkanal by hydrating an unsaturated aldehyde with a solution in the presence of a catalyst promoting a hydration reaction, wherein alcohol is added in said reaction step.

2. The process as defined in claim 1, wherein an adding amount of said alcohol with respect to said unsaturated aldehyde is in a range between 0.001 percent by weight and 10 percent by weight.

3. The process as defined in claim 1, wherein said alcohol is a dihyddric alcohol.

4. The process as defined in claim 1, wherein said unsaturated aldehyde is expressed by Formula (I) below, where R represents one of a hydrogen atom and a hydrocarbon group having up to five carbons.

5. The process as defined in claim 1, wherein a product made by hydrogenating the hydrated unsaturated aldehyde is an alcohol that is identical to said alcohol added in said reaction step in claim 1.

6. The process as defined in claim 1, wherein said unsaturated aldehyde is acrolein.

7. The process as defined in claim 6, wherein said alcohol is 1,3-propanediol.

8. The process as defined in claim 1, wherein said catalyst is an ion exchange resin.

9. The process as defined in claim 8, wherein said ion exchange resin carries lead.

10. The process as defined in claim 1, wherein said catalyst is a copolymer of an acrylic acid with diallylamineethanethiol.

11. The process as defined in claim 1, wherein said alcohol is an alcohol produced by hydrating said unsaturated aldehyde to obtain a hydrated unsaturated aldehyde followed by hydrogenating the hydrated unsaturated aldehyde.

\* \* \* \* \*